(12) United States Patent
Fishel

(10) Patent No.: US 11,357,512 B2
(45) Date of Patent: Jun. 14, 2022

(54) MECHANISM AND DEVICE FOR LEFT ATRIAL APPENDAGE OCCLUSION WITH ELECTRICAL ISOLATION

(71) Applicant: Robert Fishel, Delray Beach, FL (US)

(72) Inventor: Robert Fishel, Delray Beach, FL (US)

(*) Notice: Subject to any disclaimer, the term of this patent is extended or adjusted under 35 U.S.C. 154(b) by 680 days.

(21) Appl. No.: 15/977,202

(22) Filed: May 11, 2018

(65) Prior Publication Data

US 2022/0087683 A1 Mar. 24, 2022

Related U.S. Application Data

(60) Provisional application No. 62/505,155, filed on May 12, 2017.

(51) Int. Cl.
*A61B 17/12* (2006.01)
*A61M 25/00* (2006.01)
(Continued)

(52) U.S. Cl.
CPC .. *A61B 17/12122* (2013.01); *A61B 17/12031* (2013.01); *A61B 17/12036* (2013.01); *A61B 17/12131* (2013.01); *A61M 25/0075* (2013.01); *A61B 2017/00243* (2013.01); *A61B 2017/00893* (2013.01); *A61B 2017/12095* (2013.01); *A61B 2217/005* (2013.01); *A61M 25/0662* (2013.01); *A61M 25/09* (2013.01); *A61M 2025/0076* (2013.01); *A61M 2202/0484* (2013.01); *A61M 2202/206* (2013.01); *A61M 2210/125* (2013.01)

(58) Field of Classification Search
CPC ...... A61M 25/0075; A61M 2025/1054; A61M 2025/0076; A61M 25/0662; A61M 25/09; A61B 17/12122; A61B 17/12031; A61B 17/12131; A61B 17/12036; A61B 2017/00243
See application file for complete search history.

(56) References Cited

U.S. PATENT DOCUMENTS 4,364,392 A * 12/1982 Strother ............. A61B 17/0057
606/195
7,620,476 B2 11/2009 Morse et al.
(Continued)

FOREIGN PATENT DOCUMENTS

CN 106208276 A 12/2016
EP 2366964 A1 9/2011
(Continued)

OTHER PUBLICATIONS

International Search Report and Written Opinion issued in International Application No. PCT/US2021/053144 dated Dec. 10, 2021, 10 pages.

(Continued)

*Primary Examiner* — Jenna Zhang
(74) *Attorney, Agent, or Firm* — Brown Rudnick LLP

(57) ABSTRACT

Left atrial appendage (LAA) occlusion device including a membrane, a plurality of fixation splines and a deployment hub, the plurality of fixation splines for affixing the LAA occlusion device to an ostium of the LAA, the deployment hub being positioned in the membrane, the deployment hub including a threaded aperture and a one-way valve, for enabling a toxin to be entered into the LAA through the deployment hub.

24 Claims, 7 Drawing Sheets

(51) Int. Cl.
  *A61B 17/00* (2006.01)
  *A61M 25/09* (2006.01)
  *A61M 25/06* (2006.01)

(56) References Cited

U.S. PATENT DOCUMENTS

| | | |
|---|---|---|
| 8,500,918 B1 | 8/2013 | Meller et al. |
| 9,080,791 B1 | 7/2015 | Meller et al. |
| 9,130,502 B1 | 9/2015 | Aly et al. |
| 9,455,665 B1 | 9/2016 | Meller et al. |
| 9,931,009 B2 | 4/2018 | Miyake et al. |
| 10,391,637 B2 | 8/2019 | Miyake et al. |
| 2003/0120337 A1* | 6/2003 | Van Tassel ....... A61B 17/12172 623/1.36 |
| 2003/0220667 A1* | 11/2003 | van der Burg ... A61B 17/12022 606/200 |
| 2005/0288706 A1* | 12/2005 | Widomski ......... A61B 17/0057 606/213 |
| 2007/0142964 A1 | 6/2007 | Abramson |
| 2008/0011288 A1 | 1/2008 | Olsson |
| 2008/0140255 A1 | 6/2008 | Ziegler et al. |
| 2009/0049640 A1 | 2/2009 | Lee et al. |
| 2012/0040179 A1 | 2/2012 | Dave |
| 2013/0018413 A1 | 1/2013 | Oral et al. |
| 2013/0138138 A1 | 5/2013 | Clark et al. |
| 2013/0234645 A1 | 9/2013 | Goei et al. |
| 2014/0277074 A1 | 9/2014 | Kaplan et al. |
| 2014/0350592 A1* | 11/2014 | Kreidler ............. A61B 17/1215 606/200 |
| 2014/0379020 A1 | 12/2014 | Campbell et al. |
| 2015/0133989 A1 | 5/2015 | Lubock et al. |
| 2015/0229265 A1 | 8/2015 | Morita et al. |
| 2015/0236640 A1 | 8/2015 | Miyake et al. |
| 2015/0272413 A1 | 10/2015 | Miyake et al. |
| 2016/0074043 A1 | 3/2016 | Friedman et al. |
| 2016/0332748 A1 | 11/2016 | Wang |
| 2017/0095257 A1 | 4/2017 | Miller et al. |
| 2017/0100112 A1 | 4/2017 | van der Burg et al. |
| 2017/0164797 A1 | 6/2017 | Abramson et al. |
| 2017/0281193 A1 | 10/2017 | Asirvatham et al. |
| 2018/0054156 A1 | 2/2018 | Lokey |
| 2018/0338767 A1* | 11/2018 | Dasnurkar ....... A61B 17/12172 |

FOREIGN PATENT DOCUMENTS

| | | | |
|---|---|---|---|
| EP | 3636171 A1 | 4/2020 | |
| FR | 3022360 A1 | 12/2015 | |
| WO | WO-0130268 A1 * | 5/2001 | ......... A61B 17/0057 |
| WO | 2010/003115 A1 | 1/2010 | |
| WO | 2014/196480 A1 | 12/2014 | |
| WO | 2015/152431 A1 | 10/2015 | |
| WO | 2018/228383 A1 | 12/2018 | |
| WO | 2019/166017 A1 | 9/2019 | |

OTHER PUBLICATIONS

International Search Report and Written Opinion of the International Searching Authority dated Apr. 5, 2018 for International Application No. PCT/US2018/015221 (17 Pages).

International Preliminary Report on Patentability for International Application No. PCT/US2018/015221, dated Apr. 12, 2019, eight (8) pages.

International Search Report issued in International Application No. PCT/US2021/053144, dated Dec. 10, 2021, 10pages.

* cited by examiner

MECHANISM AND DEVICE FOR LEFT ATRIAL APPENDAGE OCCLUSION WITH ELECTRICAL ISOLATION

FIELD OF THE DISCLOSED TECHNIQUE

The disclosed technique relates to left atrial appendage occlusion, in general, and to methods and system for occluding as well as electrically isolating the left atrial appendage, in particular.

BACKGROUND OF THE DISCLOSED TECHNIQUE

The left atrial appendage (herein abbreviated LAA) is a contracting sac of tissue located in the upper anterior section of the left atrium of the heart. In a normal heart, the LAA plays an important role in atrial capacitance and is a contractile structure. In certain heart diseases and arrhythmias, most notably atrial fibrillation (herein abbreviated AF), the LAA can become a source for blood pooling and subsequent thrombus and embolus (i.e., blood clot) formation and embolization. AF is characterized by a rapid and irregular beating of the atria, which can lead to blood to move back and forth between the ventricles and the atria, leading to the formation of blood clots and thrombi in the LAA. Such blood clots can eventually leave the LAA and enter the blood stream, causing blockages in the passages or organs of the body (medically referred to as an embolization). Thrombus formation in the LAA accounts for the majority of cardio-embolic events, such as strokes, in patients with AF. Reference is now made to FIG. 1, which is a schematic illustration of a heart showing the formation of a blood clot, generally referenced 10, as is known in the art. FIG. 1 shows a heart with a right atrium (herein abbreviated RA) 12, a right ventricle (herein abbreviated RV) 14, a left atrium (herein abbreviated LA) 16 and a left ventricle (herein abbreviated LV) 18. An LAA 20 is shown protruding from LA 16. A mitral valve 26 controls the blood flow between LA 16 and LV 18. Blood in the heart normally flows from RA 12 to RV 14 and from LA 16 to LV 18. In a patient suffering from AF, due to the irregularities of when mitral valve 26 opens and closes, blood from LV 18 may travel back to LA 16, as shown by an arrow 22. This blood may then travel to LAA 20 and form a thrombus 24, which can eventually pass through mitral valve 26 in LV 18 and then into the blood stream of the patient.

Known in the prior art are a series of devices which have been developed whose purpose is to occlude the LAA and thus prevent thrombus formation in the LAA and possible future embolization. Typically such devices have a semi-permeable filter on their face and are deployed via catheter to the opening of the LAA where they are deployed. After device deployment, through the natural process of endothelialization, the filter becomes covered with endothelium thus sealing off the LAA and isolating this source of emboli. Other devices are known which clamp or physically close the opening of the LAA thus preventing the entry of blood and the possibility of thrombus formation. Examples are such devices are shown in US patent application publication numbers 2017/0100112, 2017/0095257, 2016/0074043, 2015/0133989, 2014/0379020, 2014/0277074 and 2013/0138138.

All prior art devices developed to date while being generally effective in mechanically isolating the LAA from the left atrium fail to electrically isolate this structure from the left atrium. Therefore arrhythmias such as AF originating in the LAA can still conduct into the remainder of the heart and can cause health issues. Studies have shown that in certain patients with AF, the LAA is the major driver of the arrhythmia and isolation or amputation of the LAA will control or help to control the underlying cardiac arrhythmia. For example, approximately one third of patients who undergo LAA amputation at the time of mitral valve repair are found to have spontaneous resolution of otherwise previously persistent AF on post-operative follow-up. Many patients who undergo LAA occlusion device placement are still symptomatic with the underlying arrhythmia, such as AF, and while the stroke risk is decreased after the LAA has been occluded, the patient nonetheless remains symptomatic of AF.

What is needed is therefore a method and system for occluding the LAA while also electrically isolating it such that emboli formation is prevented and AF originating from the LAA is eliminated.

SUMMARY OF THE DISCLOSED TECHNIQUE

The disclosed technique provides for a novel LAA occlusion device with electrical isolation and a novel method for occluding the LAA and isolating it electrically from the rest of the heart, which overcome the disadvantages of the prior art.

According to an aspect of the disclosed technique, there is thus provided a left atrial appendage (LAA) occlusion device including a membrane, a plurality of fixation splines and a deployment hub. The deployment hub includes a threaded aperture and a one-way valve. The deployment hub is positioned in the membrane. The fixation splines are for affixing the LAA occlusion device to an ostium of the LAA. The one-way valve is for enabling a toxin to be entered into the LAA through the deployment hub.

According to another aspect of the disclosed technique, there is thus provided a left atrial appendage (LAA) occlusion device including a membrane, a plurality of fixation splines and a deployment hub. The deployment hub is positioned in the membrane. The deployment hub includes a threaded aperture, a lumen, a semi-permeable membrane and a timed drug release mechanism. The fixation splines are for affixing the LAA occlusion device to an ostium of the LAA. The lumen is for housing a toxin and the semi-permeable membrane is for covering a proximal end of the lumen of the deployment hub.

According to a further aspect of the disclosed technique, there is thus provided a left atrial appendage (LAA) occlusion device including a membrane and a deployment hub. The membrane is for covering an ostium of the LAA and the deployment hub is positioned in the membrane. The deployment hub includes a one-way valve for enabling a toxin to be entered into the LAA through the deployment hub. The membrane is held in place over the ostium via a holding mechanism.

According to another aspect of the disclosed technique, there is thus provided a fluid activated timed drug release mechanism including a deployment hub, a molecular sieve and a glue. The deployment hub is for housing a target drug and a fluid activated glue-dissolving enzyme. The molecular sieve is positioned over a proximal side of the deployment hub and the glue is positioned over a distal side of the deployment hub. The molecular sieve is for enabling a fluid to enter the deployment hub. The molecular sieve enables the fluid to enter the deployment hub for activating the fluid activated glue-dissolving enzyme. The fluid activated glue-dissolving enzyme dissolves the glue thereby enabling the target drug to be released via the distal side.

According to a further aspect of the disclosed technique, there is thus provided a method for deploying a left atrial appendage (LAA) occlusion system in a patient. The LAA occlusion system includes a membrane and a deployment hub positioned in the membrane. The method includes the procedures of inserting a guidewire into the patient for accessing a right atrium of a heart of the patient and puncturing a transseptal point in the heart for enabling access to the LAA. The method also includes the procedures of moving an injection tube loaded with the LAA occlusion system over the guidewire such that the LAA occlusion system is within the LAA and deploying the LAA occlusion system such that the membrane is affixed to tissue forming an ostium of the LAA. The method further includes the procedures of injecting a toxin via the injection tube into the LAA through a one-way valve of the deployment hub and inserting an isolation device and a delivery sheath over the injection tube. The method also includes the procedures of positioning the isolation device and the delivery sheath to tissue surrounding the ostium of the LAA and pulling back the delivery sheath such that an expandable section of the isolation device expands around the tissue surrounding the ostium. The method further includes the procedures of temporarily coupling the isolation device with an area around a vestibule of the LAA thereby forming a lumen around the LAA, releasing the injection tube from the LAA occlusion system and releasing the toxin into the lumen around the LAA via the injection tube. The method finally includes the procedures of removing the injection tube and inserting a suction tube over the guidewire, removing the toxin in the lumen around the LAA with the suction tube and removing the delivery sheath, the isolation device and the guidewire.

BRIEF DESCRIPTION OF THE DRAWINGS

The disclosed technique will be understood and appreciated more fully from the following detailed description taken in conjunction with the drawings in which.

DETAILED DESCRIPTION OF THE EMBODIMENTS

The disclosed technique overcomes the disadvantages of the prior art by providing an occlusion device and system which is deployed at the ostium (i.e., opening) of the LAA. The occlusion device has either a semi-permeable or impermeable membrane for covering the ostium of the LAA and may have a plurality of fixation splines for holding the occlusion device in place. The occlusion device may also be held in place using staples and/or a glue. The occlusion device may further be held in place using an additional device such as a balloon catheter. Once deployed, the LAA is physically isolated from the LA. The occlusion device also includes a hollow central deployment hub, embodied as a one-way valve, such as a diaphragm valve, for injecting a toxin or drug into the LAA. Following device deployment, a drug or toxin is infused via the deployment hub into the endoluminal appendage space of the LAA for killing the tissue therein and thus electrically isolating the LAA from the rest of the heart. The drug or toxin can be embodied as any biological inhibitor of cellular function, such as a viral vector, a drug, a medication and the like. In one embodiment of the disclosed technique, an isolation device and delivery sheath is also included for applying the drug or toxin to the tissue surrounding the ostium of the LAA as well. The delivery sheath holds the isolation device in a contracted form. Once positioned at the ostium of the LAA, the delivery sheath is pulled back thus releasing the isolation device which expands to cover the tissue surrounding the ostium of the LAA. A drug or toxin can then be applied to that tissue for killing it as well and electrically isolating that tissue from the rest of the heart.

In another embodiment of the disclosed technique, the deployment hub includes a drug delivery timed release device for housing a drug or toxin which is only released once endothelialization of the occlusion has occurred. In this embodiment, one end of the deployment hub includes a semi-permeable membrane for enabling a fluid to enter the deployment hub. The other end includes a fluid activated glue-dissolving enzyme which dissolves when sufficient fluid comes in contact with it. The glue-dissolving enzyme covers the end of the occlusion device facing the LAA. The amount of enzyme placed is selected such that the enzyme will dissolve from fluid entering the semi-permeable membrane after sufficient time has passed for endothelialization of the occlusion device.

Figure 2A:
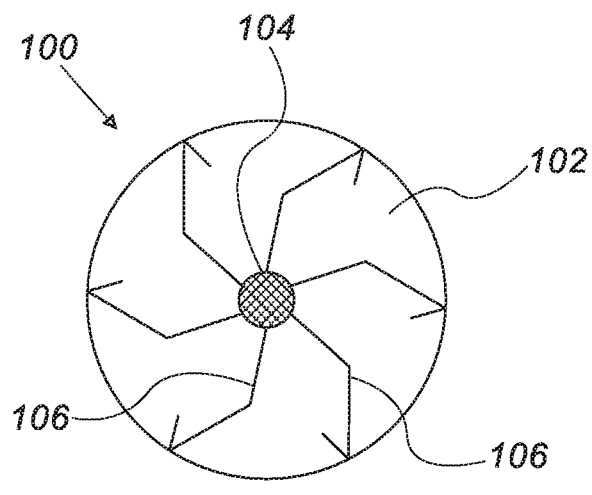
FIGS. 2A and 2B are schematic illustrations of a first and second embodiment of an LAA occlusion device, constructed and operative in accordance with an embodiment of the disclosed technique.
Figure 2B:
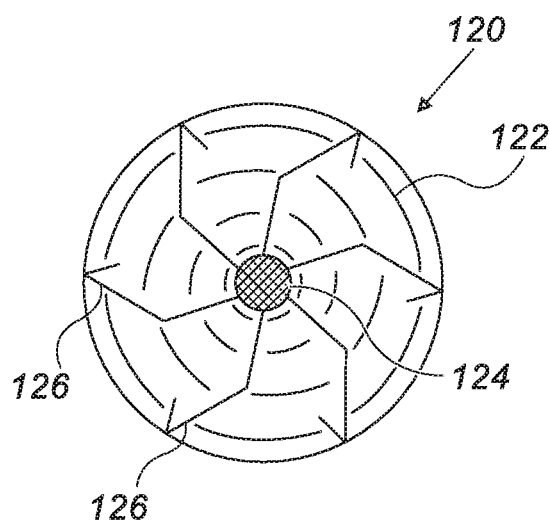

Reference is now made to FIGS. 2A and 2B, which are schematic illustrations of a first and second embodiment of an LAA occlusion device, generally referenced 100 and 120 respectively, constructed and operative in accordance with an embodiment of the disclosed technique. With reference to FIG. 2A, LAA occlusion device 100 includes a membrane 102, a central deployment hub 104 and a plurality of fixation splines 106. Membrane 102 may be embodied as an impermeable membrane or a semi-permeable membrane. As a semi-permeable membrane, membrane 102 may be semi-permeable in only one direction, thus letting liquids pass through the membrane in only one direction. In the case of membrane 102 being an impermeable membrane, membrane 102 is completely closed such that fluid cannot cross through it. In such a case, the LAA may need to be drained of blood, or at least some of the blood therein before the toxin or drug is injected since otherwise the existing blood volume in the LAA will have nowhere to go. In the case of membrane 102 being a semi-permeable membrane, membrane 102 may have poor semi-permeability. Membrane 102 may have the shape of a parachute, an umbrella, may be circular in shape, may have a balloon shape or may have any shape that approximates the anatomy of the ostium of the LAA. Central deployment hub 104 includes a one-way valve (not shown) as well as a threaded aperture (not shown). Central deployment hub 104 can also be referred to as a deployment port. The one-way valve can be used for injecting a drug or toxin into the LAA once deployed. The one-way valve can be embodied as a perforable yet sealable membrane, a sealable polymer membrane, a membrane with a one-way mechanism and the like. Membrane 102 is constructed as to keep the drug or toxin local to the LAA, thereby effectively killing the tissue of the LAA while not affecting other tissue of the heart. In the case of membrane 102 being a semi-permeable membrane, a small amount of the drug or toxin may seep out of the LAA via the membrane in the case when the drug or toxin is released before endothelialization has occurred. This also enables blood to seep out of the LAA. Even though the drug or toxin may seep out, for example in the case of ethanol being the drug, the drug will mix with the blood in the heart and will end up being diluted thus not causing any damage to the heart outside the LAA. The toxin or drug injected into the LAA however will permeate the LAA undiluted and perform its functions of killing the cells inside the LAA. The threaded aperture enables a catheter or delivery device to be attached to LAA occlusion device 100 for placement in the LAA. Once deployed, the catheter or delivery device can be unscrewed thus leaving the LAA occlusion device in place. Plurality of fixation splines 106 are made from a biocompatible metal and may be designed to have a closed and open shape. Plurality of fixation spines 106 are arranged radially around central deployment hub 104. Plurality of fixation splines 106 are used to position and hold LAA occlusion device 100 in the ostium of the LAA while the natural process of endothelialization occurs. Plurality of fixation splines 106 may also be formed in a spring shape held under pressure by a delivery sheath such that when the delivery sheath is removed, the fixation splines open membrane 102 into an umbrella shape, a parachute shape, a circular shape, a balloon shape or a shape which approximates the anatomy of the ostium of the LAA. In the case of membrane 102 being embodied as a semi-permeable membrane, any blood located in the LAA can seep out of the LAA via the semi-permeable membrane into the LA. This may also be the case when the drug or toxin is released into the LAA before endothelialization occurs, with small amounts of blood mixed with the drug or toxin seeping through the semi-permeable membrane into the LA. If the semi-permeability of membrane 102 in this embodiment is only in one direction, then blood in the LA cannot enter the LAA, however blood and/or the drug or toxin can seep out of the LAA into the LA before endothelialization occurs.

In another embodiment of the disclosed technique the LAA occlusion device may only include a membrane and a central deployment hub, not having any fixation splines. In this embodiment (not shown), other elements may be used to hold the LAA occlusion device in place while the toxin or drug is injected into the LAA. For example, in one embodiment, staples may be used to affix the membrane to the ostium of the LAA. In another embodiment, a glue may be used to affix the membrane to the ostium of the LAA. In yet a further embodiment, a balloon catheter or other type of soft catheter can be inserted behind the LAA occlusion device and inflated once the LAA occlusion device is in place, thereby holding the LAA occlusion device at the ostium of the LAA while the drug or toxin is injected into the LAA.

With reference to FIG. 2B, LAA occlusion device 120 includes a semi-permeable membrane 122, a central deployment hub 124 and a plurality of fixation splines 126. Semi-permeable membrane 122 may allow small amounts of fluid to cross it, thus once positioned in the ostium of the LAA, semi-permeable membrane 122 may allow blood to cross from the LAA to the LA and vice-versa, however any blood clots formed in the LAA will remain there. Semi-permeable membrane 122 may be designed as a very fine sieve. All other aspects of LAA occlusion device 120 are identical to LAA occlusion device 100.

In either LAA occlusion device, a catheter or delivery tube can be coupled with (for example, screwed into the threaded aperture) the central deployment hub for injecting a drug, toxin, medication or therapeutic agent into the LAA for killing the cardiac tissue of the LAA. A possible drug which can be used to kill the tissue of the LAA is ethanol mixed with X-ray contrast. In general, ethanol is toxic to cardiac tissue in high concentrations, thus a high concentration of ethanol should be injected into the LAA to kill the tissue. However in lower concentrations, ethanol is not toxic to cardiac tissue. Therefore, if ethanol leaks out of the LAA into the LA and the heart and the blood stream, the flow of blood into the heart should dilute the ethanol to concentrations which are not toxic to the patient. As mentioned above, the drug or toxin can be any biological inhibitor of cellular function, such as a drug, a medication, a viral vector and the like.

Figure 3:
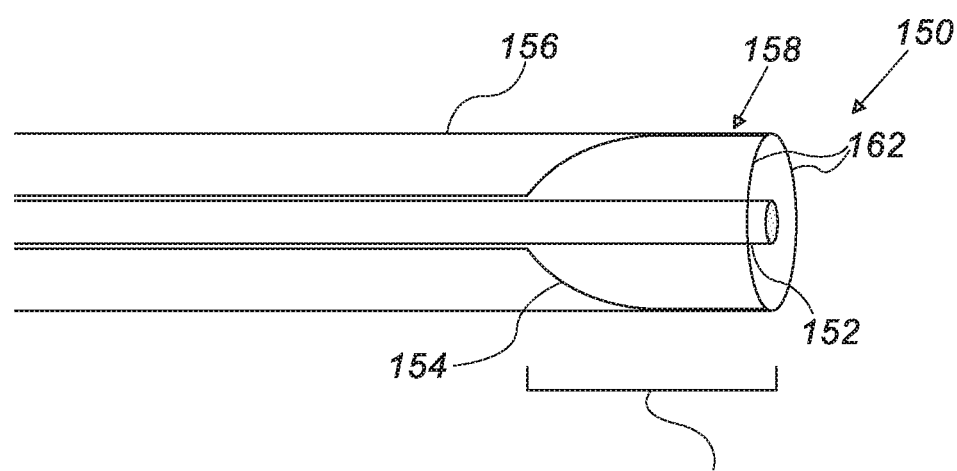
FIG. 3 is a schematic illustration of an isolation device and a delivery sheath, constructed and operative in accordance with another embodiment of the disclosed technique.

Reference is now made to FIG. 3, which is a schematic illustration of an isolation device and a delivery sheath, generally referenced 150, constructed and operative in accordance with another embodiment of the disclosed technique. FIG. 3 shows an injection tube 152, an isolation device 154 and a delivery sheath 156. Injection tube 150 can be used for injecting a drug or toxin into the LAA via the occlusion devices shown in FIGS. 2A and 2B. Injection tube 150 can also be used for injecting a drug or toxin into the tissue around the ostium of the LAA. Isolation device 154 is an expandable membrane which is held in place by delivery sheath 156. Isolation device 154 may be embodied as a filter basket or sheath, similar to the impermeable or semi-permeable membranes of the LAA occlusion devices shown in FIGS. 2A and 2B. Isolation device 154 and delivery sheath 156 may be deployed via the same delivery system used to deploy the LAA occlusion device of FIGS. 2A and 2B into the region of the antrum or vestibule of the area around the LAA.

Isolation device 154 includes an expandable section 160 which is held flush against the inner edges of delivery sheath 156, as shown by an arrow 158. Edges 162 of isolation device 154 may include grips, suction bulbs or other mechanisms (not shown) for temporarily coupling isolation device 154 with the tissue surrounding the ostium of the LAA. After deployment of the LAA occlusion device, isolation device 154 and delivery sheath 156 may be deployment over the LAA occlusion device. Delivery sheath 156 is then pulled back, enabling isolation device 154 to expand and substantially cover the tissue surrounding the ostium of the LAA.

In one embodiment of the disclosed technique, isolation device 154 is used to ensure that any drug or toxin applied to the LAA which might leak out does not enter the LA, the heart or the circulatory system. In another embodiment of the disclosed technique, once isolation device is deployed, injection tube 152 may be pulled back slightly such that the drug and toxin can be applied to the tissue around the ostium of the LAA by filling up the lumen formed by the isolation device. Isolation device 154 thus ensures that the injected drug or toxin does not enter the LA or the heart or blood stream. After the toxin has destroyed the tissue surrounding the ostium of the LAA, which may take about 10-15 minutes, injection tube 152 can be removed and a vacuum tube can be inserted to vacuum out the drug or toxin before delivery sheath 156 and isolation device 154 are removed.

Figure 1:
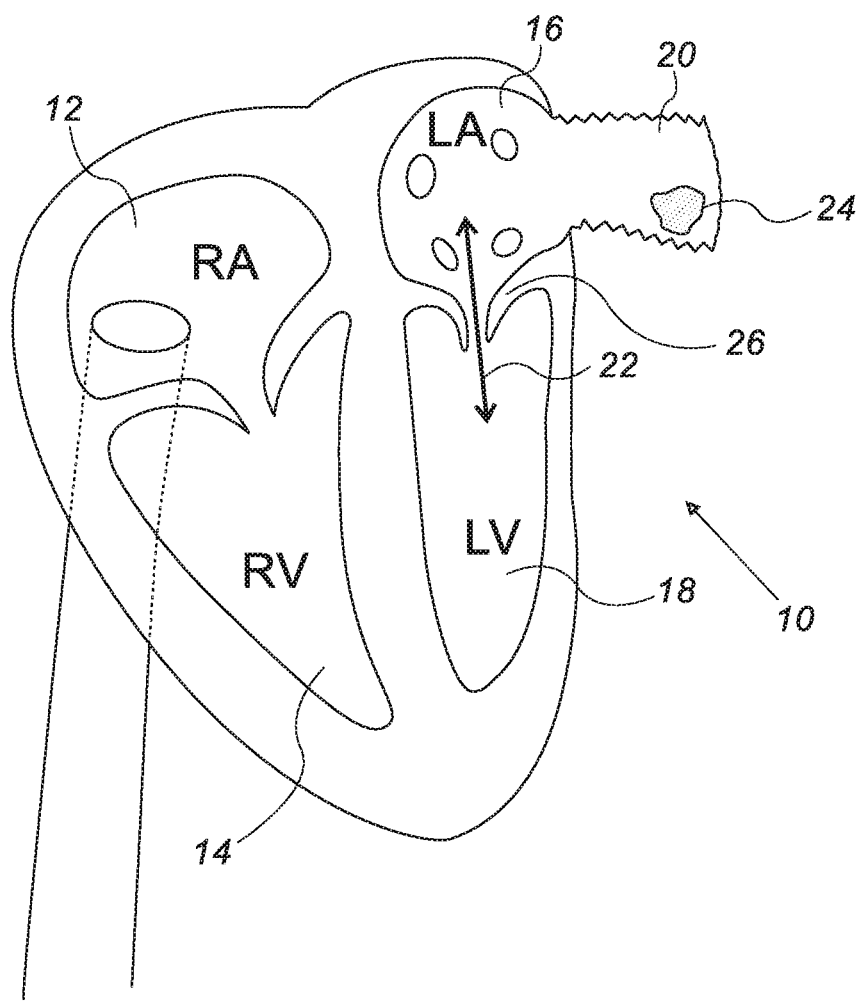
FIG. 1 is a schematic illustration of a heart showing the formation of a blood clot, as is known in the art.
Figure 4:
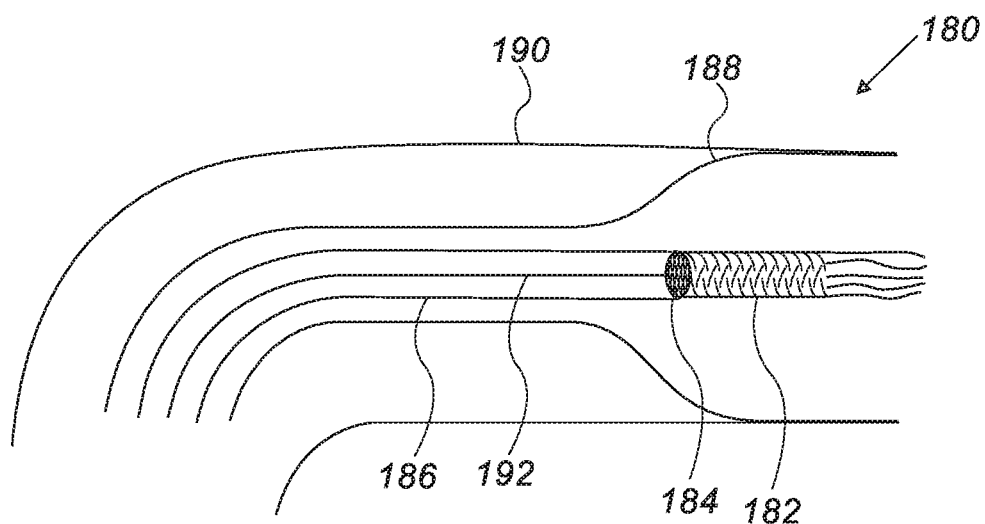
FIG. 4 is a schematic illustration of an LAA occlusion system, constructed and operative in accordance with a further embodiment of the disclosed technique.

Reference is now made to FIG. 4, which is a schematic illustration of an LAA occlusion system, generally referenced 180, constructed and operative in accordance with a further embodiment of the disclosed technique. LAA occlusion system 180 includes an LAA occlusion device 182, an injection tube 186, an isolation device 188 and a delivery sheath 190. LAA occlusion device 182 is coupled with injection tube 186 via a threaded aperture 184 in occlusion device 182. In another embodiment of the disclosed technique (not shown), LAA occlusion device 182 may be coupled with injection tube 186 via a glue, staples or via an inflated balloon catheter and not via a threaded aperture. LAA occlusion device 182 can be either one of LAA occlusion devices 100 (FIG. 2A) or 120 (FIG. 2B) and is shown in FIG. 4 in a contracted state. Isolation device 188 and delivery sheath 190 are substantially similar to the isolation device and delivery sheath shown above in FIG. 3. A guidewire 192 may be used initially to locate the ostium of the LAA after which the other elements of LAA occlusion system 180 are deployed to the LAA.

Figure 5A:
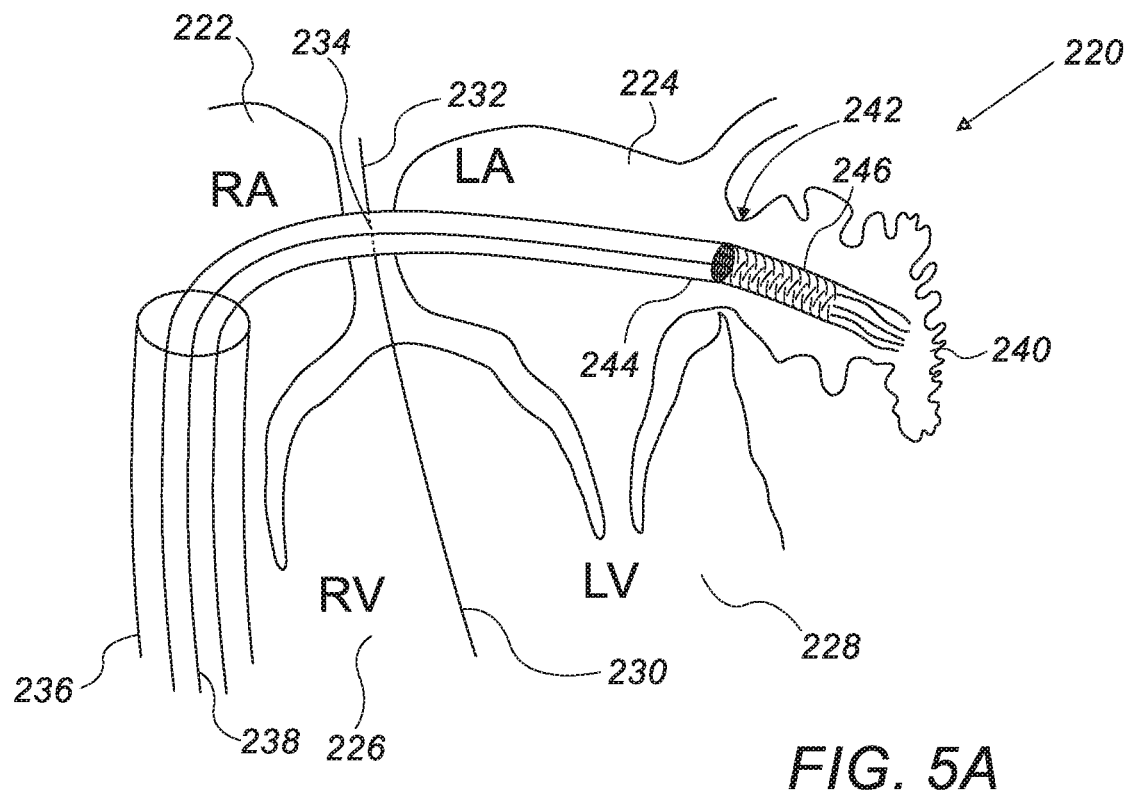
FIGS. 5A-5F are schematic illustrations of the deployment of the LAA occlusion system of FIG. 4 in a patient, constructed and operative in accordance with another embodiment of the disclosed technique.

Reference is now made to FIGS. 5A-5F, which are schematic illustrations of the deployment of the LAA occlusion system of FIG. 4 in a patient, generally referenced 220, constructed and operative in accordance with another embodiment of the disclosed technique. Identical elements in these figures are labeled using identical reference numbers. Not all elements are labeled in every figure in order to keep the figures from being too cluttered. With reference to FIG. 5A, shown is a section of the heart, including an RA 222, an RV 226, an LA 224 and an LV 228. A septum 230 separates the left side and right side of the heart. Shown as well is an LAA 240, an inferior vena cava 236 which leads into RA 222, an interatrial septum 232 and a fossa ovalis 234. The entrance or ostium of LAA 240 is shown via an arrow 242. A guidewire 238 is inserted into a patient via the right femoral artery (not shown) or other artery which links up with inferior vena cava 236, thus gaining access to RA 222. Guidewire 238 is used to puncture fossa ovalis 234, or at another transseptal puncture point, thus enabling access to LA 224 and LAA 240. An injection tube 244, loaded with an LAA occlusion device 246 of the disclosed technique, is then moved over guidewire 238 until LAA occlusion device 246 is within LAA 240.

Figure 5B:
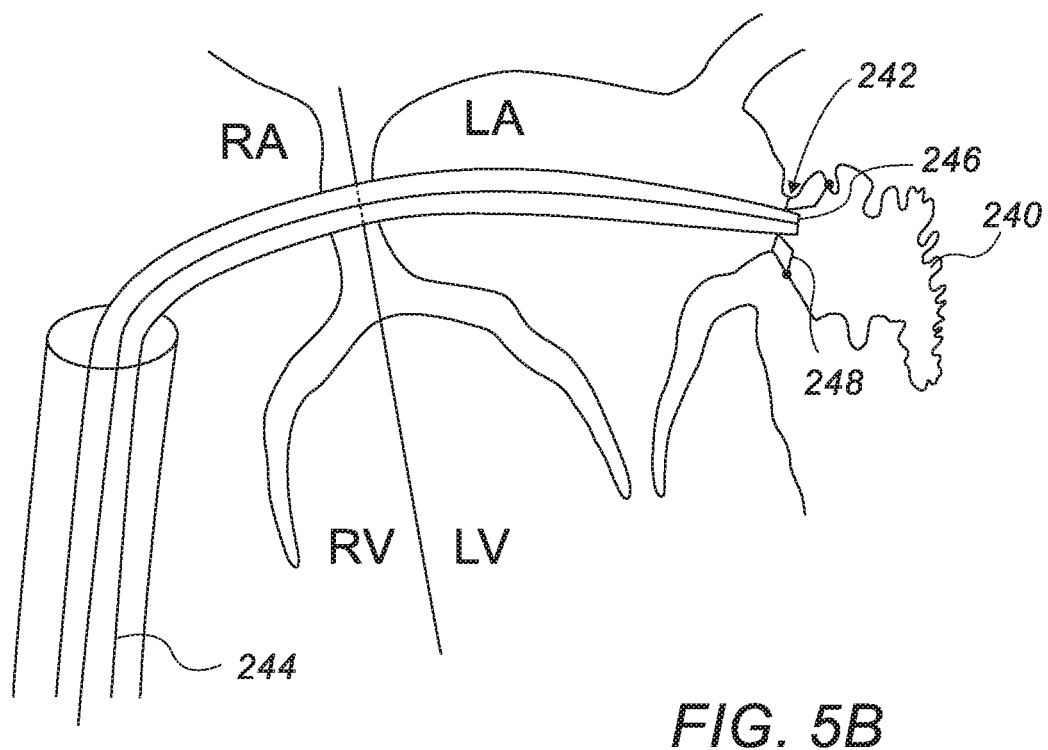
Figure 5D:
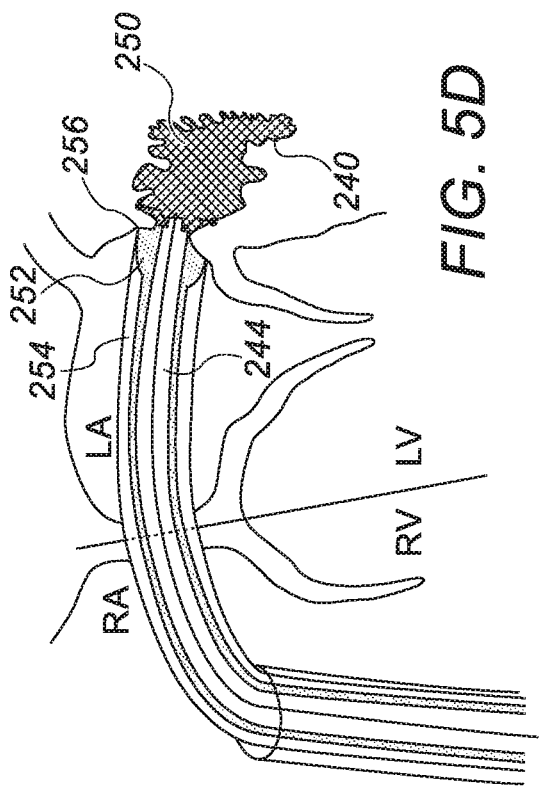
Figure 5F:
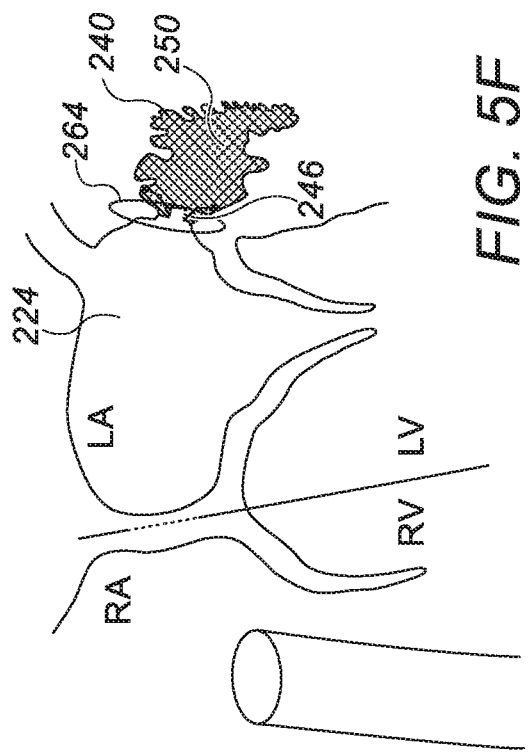
Figure 5C:
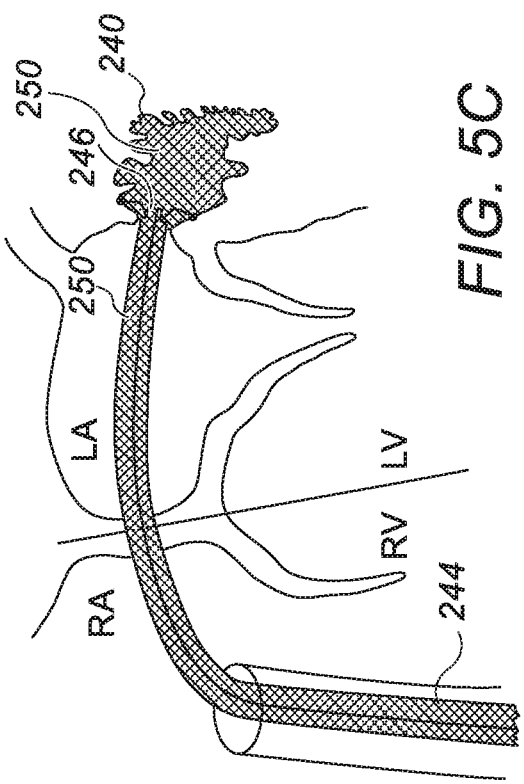
Figure 5E:
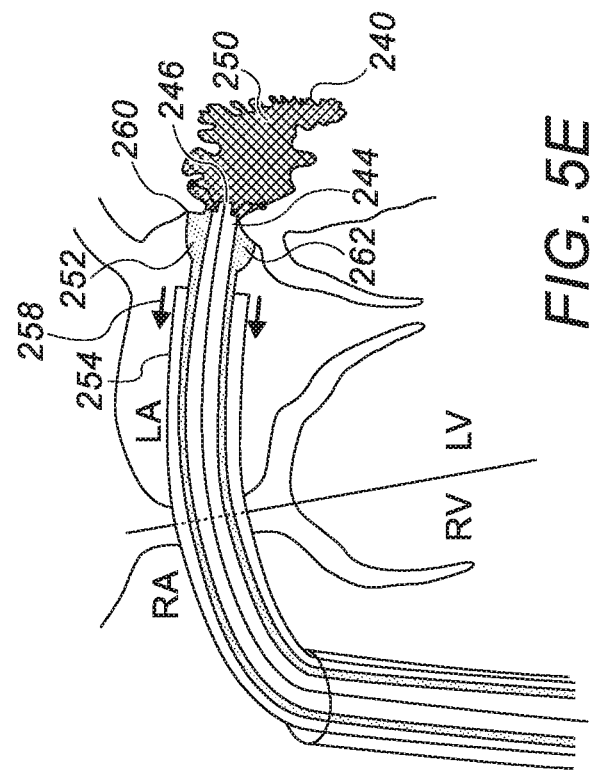

With reference to FIG. 5B, LAA occlusion device 246 is deployed such that a plurality of fixation splines 248 affix LAA occlusion device 246 to the tissue forming the ostium of LAA 240. With reference to FIG. 5C, once properly deployed and firmly in place, a drug, toxin, therapeutic agent or medication 250 is injected via injection tube 244 into LAA 240. Drug 250 is injected into LAA 240 via the one-way valve (not shown) of LAA occlusion device 246. Once injected, drug 250 kills the tissue of LAA 240 such that it is no longer electrically active, thus elimination LAA 240 as a source of AF in certain patients. As mentioned above, this may take between 10-15 minutes. With reference to FIG. 5D, an isolation device 252 and a delivery sheath 254 are inserted over injection tube 244 and positioned around the tissue surrounding the ostium of LAA 240. Isolation device 252 and delivery sheath 254 are positioned around the ostium of LAA 240, shown by a reference line 256. With reference to FIG. 5E, delivery sheath 254 is pulled back, as shown by a plurality of arrows 258 such that the expandable section (not labeled) of isolation device 252 expands around the tissue at the ostium of LAA 240, shown by a reference line 260. Isolation device 252 is then temporarily coupled with the area around the antrum or vestibule of LAA 240. Studies have shown that when the LAA is a source of AF, the tissue surrounding the ostium of the LAA can also be a source of AF. Therefore according to the disclosed technique, injection tube 244 is released from LAA occlusion device 246 (not shown) and drug 250 is released (not shown) into a lumen 262 formed by isolation device 252 to kill the tissue surrounding the ostium of the LAA as well. As mentioned above, injection tube 244 may then be removed and a suction tube or vacuum tube (both not shown) may be inserted to remove drug 250 from lumen 262. With reference to FIG. 5F, once the drug has been removed from the lumen formed by the isolation device, the delivery sheath, isolation device, injection tube and guidewire are removed, leaving LAA occlusion device 246 in place covering LAA 240. Within a few weeks, LAA occlusion device 246 will be covered with endothelial cells through the body's natural process of endothelialization, thus permanently leaving LAA occlusion device 246 at the ostium of LAA 240 and preventing the further formation of blood clots. As a toxin was inserted into LAA 240 to kill the cardiac tissue therein, LAA 240 is not just physically separated but also electrically isolated from LA 224, thus ceasing to be a source of AF. A region 264 of cardiac tissue surrounding the ostium of LAA 240 has also been killed by the toxin, thus also ceasing to be a source of AF in certain patients.

FIGS. 5A-5F have shown one embodiment of the deployment of the LAA occlusion system of the disclosed technique. Other deployments are possible. For example, a balloon catheter can be used to keep the LAA occlusion device held in place while the toxin is injected into the LAA, wherein the LAA occlusion device does not include a plurality of fixation splines. As another example, injection tube 244 may be used to release a glue at the ostium of the LAA for gluing the LAA occlusion device to the ostium of the LAA before the toxin or drug is released into the LAA. In such an embodiment, the LAA occlusion device also does not include or require a plurality of fixation splines.

Figure 6A:
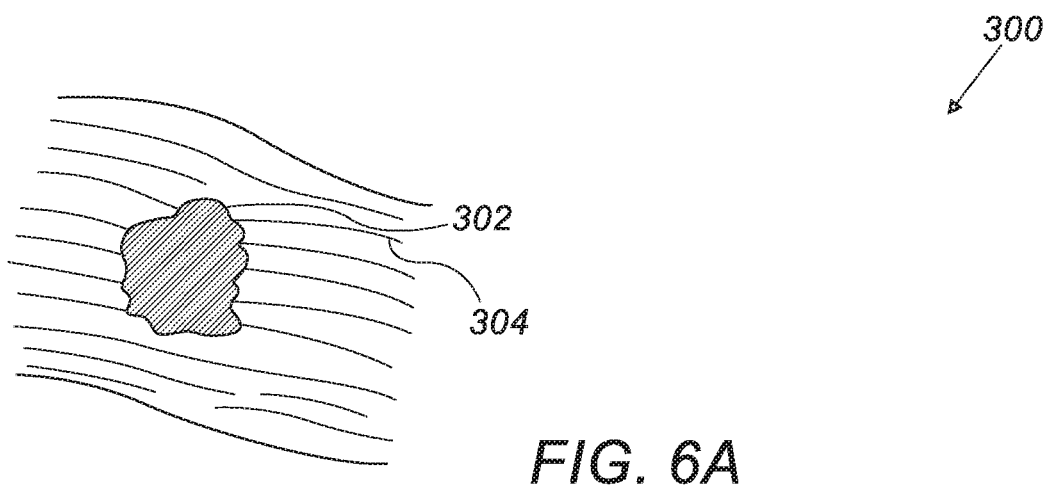
FIGS. 6A-6C are top views of the ostium of the LAA during different stages of the deployment of the LAA occlusion system of FIG. 4, constructed and operative in accordance with a further embodiment of the disclosed technique.
Figure 6B:
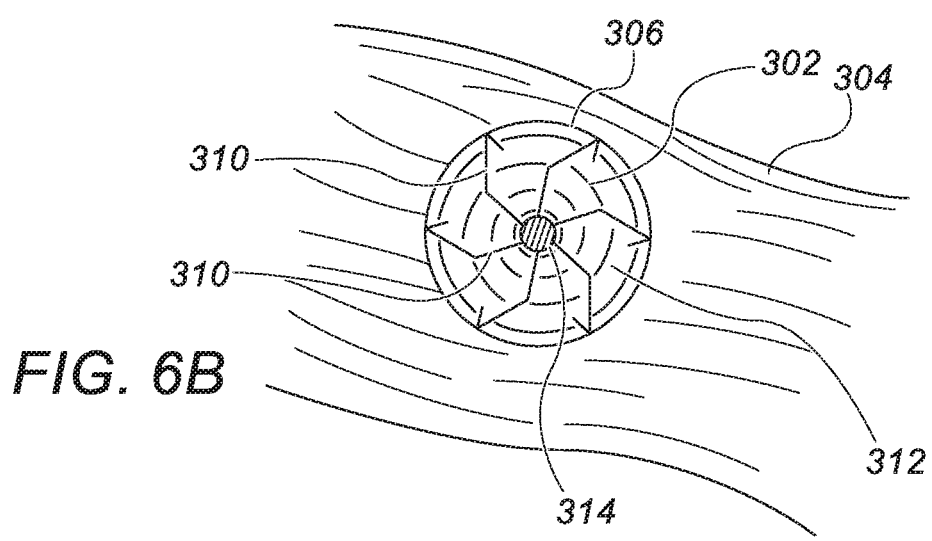
Figure 6C:
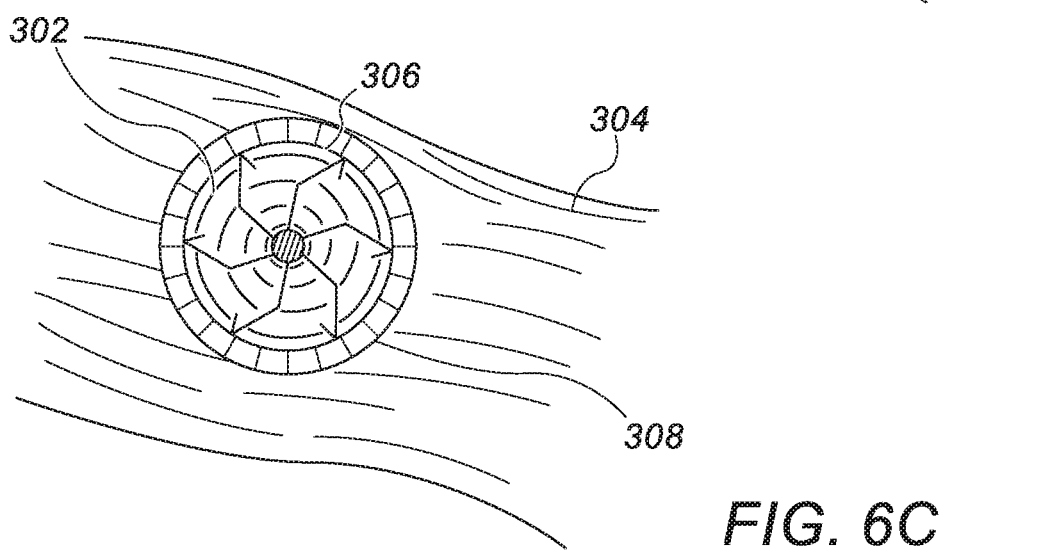

Reference is now made to FIGS. 6A-6C, which are top views of the ostium of the LAA during different stages of the deployment of the LAA occlusion system of FIG. 4, generally referenced 300, constructed and operative in accordance with a further embodiment of the disclosed technique. Identical elements in these figures are labeled using identical reference numbers. With reference to FIG. 6A, shown is a top view of the ostium of an LAA 302 and the wall of an LA 304. With reference to FIG. 6B, shown is a top view of an LAA occlusion device 306 of the disclosed technique placed over the ostium of LAA 302. Shown is the deployment of a plurality of fixation splines 310, a semi-permeable membrane 312 covering the entire ostium of LAA 302 and a central deployment hub 314 having a one-way valve and a threaded aperture. With reference to FIG. 6C, shown is a top view of LAA occlusion device 306 deployed along with the deployment of an isolation device 308. As can be seen, isolation device 308 covers a larger surface area than LAA occlusion device 306 such that not only the tissue of the LAA can be killed by a drug or toxin but also the area surrounding the ostium of the LAA.

Figure 7A:
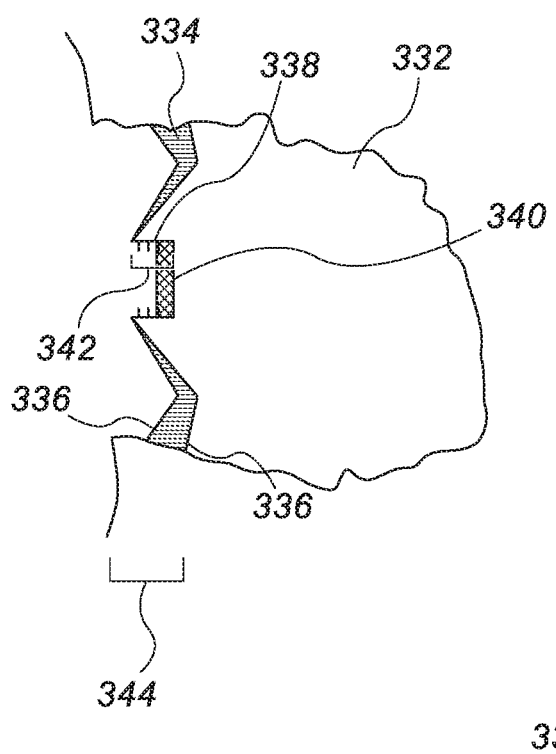
FIGS. 7A and 7B are schematic illustrations of the LAA occlusion device of FIGS. 2A and 2B being deployed at different positions within the LAA, constructed and operative in accordance with another embodiment of the disclosed technique.
Figure 7B:
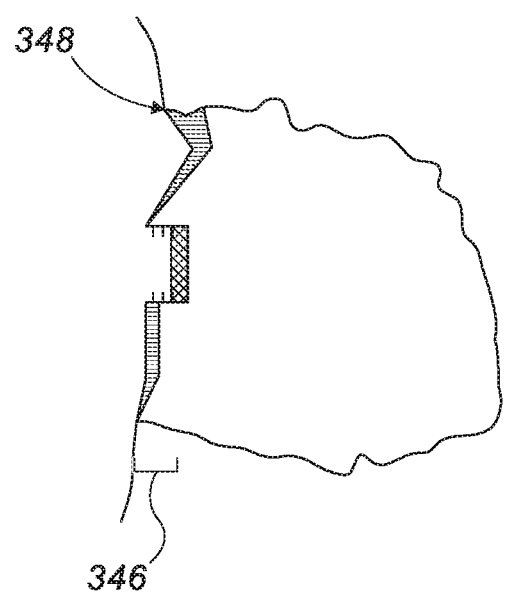

Reference is now made to FIGS. 7A and 7B, which are schematic illustrations of the LAA occlusion device of FIGS. 2A and 2B being deployed at different positions within the LAA, generally referenced 330, constructed and operative in accordance with another embodiment of the disclosed technique. A close-up view of the LAA occlusion device of the disclosed technique is shown positioned inside an LAA 332. Shown in greater detail is a semi-permeable membrane 334, a plurality of fixation splines 336, a central deployment hub 338 including a one-way valve 340 as well as a threaded aperture 342. As shown in FIG. 7A, plurality of fixation splines 336 can be positioned such that the LAA occlusion device is within LAA 332, as shown by a section 344. With reference to FIG. 7B, which shows the same LAA occlusion device, however positioned slightly differently, the plurality of fixation splines can be positioned right at the ostium of the LAA, as shown by a section 346. As shown by an arrow 348, LAA occlusion device now covers the ostium of LAA 332.

Figures 8A, 8B:
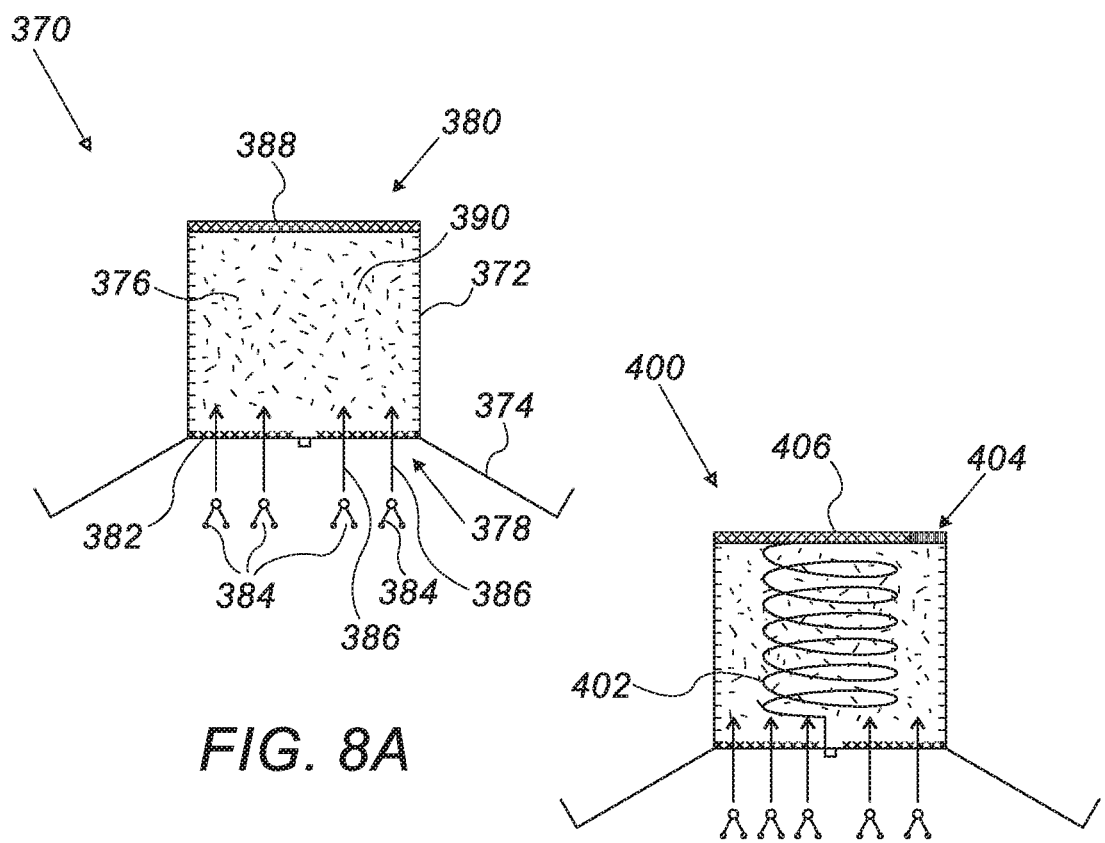
FIGS. 8A and 8B are schematic illustrations of the drug delivery mechanism of the LAA occlusion device of FIGS. 2A and 2B, constructed and operative in accordance with a further embodiment of the disclosed technique.

Reference is now made to FIGS. 8A and 8B, which are schematic illustrations of the drug delivery mechanism of the LAA occlusion device of FIGS. 2A and 2B, generally referenced 370 and 400 respectively, constructed and operative in accordance with a further embodiment of the disclosed technique. FIG. 8A shows a first embodiment of the drug delivery mechanism of the disclosed technique. As shown is a central deployment hub 372 of an LAA occlusion device, which includes a plurality of fixation splines 374. Deployment hub 372 is filled with a target drug, toxin, therapeutic agent or medication 376 as well as a fluid activated glue-dissolving enzyme 390. Target drug 376 is placed in the lumen of deployment hub 372 as a dry substance. A partial vacuum may also be applied to the lumen. Deployment hub 372 has a proximal end 378 facing the LA as well as a distal end 380 facing the LAA. Proximal end 378 is covered with a molecular sieve 382 which allows fluids, shown as a plurality of particles 384, to cross from the LA into the lumen of deployment hub 372, shown by a plurality of arrows 386. The fluid may be blood, water or other fluids normally found in the body. Distal end 380 is covered with a glue 388. Glue 388 is substantially impermeable until glue-dissolving enzyme 390 comes in contact with it. Glue 388 may be made from a biological agent which is subject to enzymatic degradation by glue-dissolving enzyme 390. Glue-dissolving enzyme 390 only becomes activated when sufficient fluid comes into contact with it. When sufficient amounts of particles 384 (i.e., the fluid) come into contact with glue-dissolving enzyme 390, the particles react with the enzyme which begins to dissolve glue 388 and allows particles to pass there through. The rate at which glue 388 dissolves is a function of a number of factors such as the concentration of the enzyme in deployment hub 372, how quickly molecular sieve 382 allows fluid to enter the lumen of deployment hub 372 and the chemistry of glue 388 and glue-dissolving enzyme 390. Adjusting these factors, the release of target drug 376, via the loss of adhesion of glue 388, can be tailored for specific time-release periods, thus enabling target drug 376 to be time-released.

Considering it takes about 4 weeks for endothelial cells to cover an LAA occlusion device, the described time-release factors of deployment hub 372 can be selected such that glue-dissolving enzyme 388 will dissolve after approximately 6 weeks, thus releasing the target drug into the LAA to kill the tissue therein. An example of a target drug may be doxorubicin (sold under the trade name Adriamycin® or Rubex®), which has a high molecular weight and is also toxic to cardiac tissue. As mentioned above, drug delivery of the target drug is activated by fluid or moisture coming into contact with the fluid activated glue-dissolving enzyme. Once the LAA occlusion device is employed, fluid passing through molecular sieve 382 will start activating glue-dissolving enzyme 390 which will begin dissolving glue 388 and slowly allowing target drug 376 to enter the LAA. As mentioned above, the factors determining when glue 388 dissolves can be adjusted such that the target drug is only released after endothelialization of the ostium of the LAA. In this embodiment of the disclosed technique, the cardiac tissue of the LAA is killed once the LAA occlusion device is deployed and fully covered by endothelial cells. As such, the LAA occlusion device is deployed and within a number of weeks of deployment, the LAA will begin to deteriorate and lose function.

Reference is now made to FIG. 8B, which shows another embodiment of the drug delivery mechanism of the disclosed technique. In this embodiment, the deployment hub includes a spring 402 and a lid 406. Lid 406 is coupled with the deployment hub by a glue 404 at only one section of lid 406. This embodiment is substantially similar to the embodiment shown in FIG. 8A in terms of elements (not labeled) and function, except that once glue 404 is dissolved, spring 402, which may be loaded into the deployment hub under pressure, pushes lid 406 open, thus enabling the target drug to enter into the endoluminal appendage space and start deteriorating the cardiac cells of the LAA.

It is noted that the drug delivery mechanism of the disclosed technique has been described relating to timed drug release in the LAA, however the drug delivery mechanism of the disclosed technique may be used in other procedures and in other locations in the body for timed drug release.

It will be appreciated by persons skilled in the art that the disclosed technique is not limited to what has been particularly shown and described hereinabove. Rather the scope of the disclosed technique is defined only by the claims, which follow.

The invention claimed is:

1. Left atrial appendage (LAA) occlusion device comprising:
   a semi-permeable membrane having semi-permeability in only one direction, for covering an ostium of said LAA; and
   a deployment hub, positioned in said semi-permeable membrane,
   wherein said deployment hub comprises a one-way valve, for enabling a toxin to be entered into said LAA through said deployment hub; and
   wherein said semi-permeable membrane enables said toxin to seep out of said LAA and prevents blood from entering said LAA.

2. The LAA occlusion device according to claim 1, wherein said semi-permeable membrane has a shape selected from the list consisting of:
   an umbrella shape;
   a parachute shape;
   a circular shape;
   a balloon shape; and
   a shape which approximates the anatomy of said ostium of said LAA.

3. The LAA occlusion device according to claim 1., wherein at least one of a catheter or a delivery tube can be coupled with said deployment hub, for providing said toxin to said deployment hub.

4. The LAA occlusion device according to claim 1, wherein said toxin is selected from the list consisting of:
   ethanol;
   a drug;
   a medication;
   a viral vector; and
   a biological inhibitor of cellular function.

5. The LAA occlusion device according to claim 1, wherein said semi-permeable membrane is configured to be held in place over said ostium via a holding mechanism.

6. The LAA occlusion device according to claim 5, wherein said holding mechanism is selected from the list consisting of:
   a plurality of staples;
   a glue; and
   a balloon catheter.

7. The LAA occlusion device according to claim 1, further comprising:
   a plurality of fixation splines, for affixing said LAA occlusion device to said ostium of said LAA,
   said deployment hub further comprising a threaded aperture.

8. The LAA occlusion device according to claim 7, wherein said threaded aperture enables at least one of a catheter and a delivery device to be coupled with said LAA occlusion device for placement in said LAA.

9. The LAA occlusion device according to claim 7, wherein said plurality of fixation splines is made from a biocompatible metal.

10. The LAA occlusion device according to claim 7, wherein said plurality of fixation splines has an open shape and a closed shape.

11. The LAA occlusion device according to claim 7, wherein said plurality of fixation splines is arranged radially around said deployment hub.

12. The LAA occlusion device according to claim 7, wherein said plurality of fixation splines is formed as a spring and is held under pressure by a delivery sheath.

13. Method for deploying a left atrial appendage (LAA) occlusion system in a patient, said LAA occlusion system comprising a membrane and a deployment hub, positioned in said membrane, comprising the procedures of:
   inserting a guidewire into said patient for accessing a right atrium of a heart of said patient;
   puncturing a transseptal point in said heart for enabling access to said LAA;
   moving an injection tube loaded with said LAA occlusion system over said guidewire such that said LAA occlusion system is within said LAA;
   deploying said LAA occlusion system such that said membrane is held to tissue forming an ostium of said LAA;
   injecting a toxin via said injection tube into said LAA through a one-way valve of said deployment hub;
   inserting an isolation device and a delivery sheath over said injection tube;
   positioning said isolation device and said delivery sheath to tissue surrounding said ostium of said LAA;
   pulling back said delivery sheath such that an expandable section of said isolation device expands around said tissue surrounding said ostium;
   temporarily coupling said isolation device with an area around a vestibule of said LAA thereby forming a lumen around said LAA;
   releasing said injection tube from said LAA occlusion system while maintaining said injection tube proximate to said lumen around said LAA;
   releasing said toxin into said lumen around said LAA via said injection tube;
   removing said injection tube from said guidewire and inserting a suction tube over said guidewire;
   removing said toxin in said lumen around said LAA with said suction tube; and
   removing said delivery sheath, said isolation device and said guidewire.

14. The method for deploying said LAA occlusion system according to claim 13, wherein said transseptal puncture point is a fossa ovalis of said heart.

15. The method for deploying said LAA occlusion system according to claim 13, wherein said tissue forming said ostium of said LAA which said membrane is located in a position selected from the list consisting of:
   within said LAA; and
   at said ostium of said LAA.

16. The method for deploying said LAA occlusion system according to claim 13, wherein said toxin is selected from the list consisting of:
   ethanol;
   a drug;
   a medication;
   a viral vector; and
   a biological inhibitor of cellular function.

17. The method for deploying said LAA occlusion system according to claim 13, wherein said procedure of deploying said LAA occlusion system comprises the sub-procedure of deploying a plurality of fixation splines in said LAA occlusion system for affixing said membrane to said tissue forming said ostium of said LAA.

18. The method for deploying said LAA occlusion system according to claim 13, wherein said procedure of deploying said LAA occlusion system comprises the sub-procedure of inserting a balloon catheter in said injection tube for holding said membrane of said LAA occlusion system in place over said tissue forming said ostium of said LAA.

19. The method for deploying said LAA occlusion system according to claim 13, wherein said procedure of deploying said LAA occlusion system comprises the sub-procedure of releasing a glue via said injection tube at said ostium of said LAA for gluing said membrane of said LAA occlusion system to said tissue forming said ostium of said LAA.

20. Method for deploying a left atrial appendage (LAA) occlusion system in a patient, said LAA occlusion system comprising a semi-permeable membrane having semi-permeability in only one direction and a deployment hub, positioned in said semi-permeable membrane, comprising the procedures of:
   inserting a guidewire into said patient for accessing a right atrium of a heart of said patient;
   puncturing a transseptal point in said heart for enabling access to said LAA;
   moving an injection tube loaded with said LAA occlusion system over said guidewire such that said LAA occlusion system is within said LAA;
   deploying said LAA occlusion system such that said semi-permeable membrane is held to tissue forming an ostium of said LAA;
   injecting a toxin via said injection tube into said LAA through a one-way valve of said deployment hub;
   removing said injection tube and said guidewire from said patient; and removing said toxin from said LAA via said semi-permeable membrane.

21. The method for deploying said LAA occlusion system according to claim 20, further comprising the procedures of:

after said procedure of injecting said toxin via said injection tube into said LAA, inserting an isolation device and a delivery sheath over said injection tube;

positioning said isolation device and said delivery sheath to tissue surrounding said ostium of said LAA;

pulling back said delivery sheath such that an expandable section of said isolation device expands around said tissue surrounding said ostium;

temporarily coupling said isolation device with an area around a vestibule of said LAA thereby forming a lumen around said LAA;

releasing said injection tube from said LAA occlusion system while maintaining it proximate to said lumen around said LAA;

releasing said toxin into said lumen around said LAA via said injection tube;

inserting a suction tube over said guidewire;

removing said toxin in said lumen around said LAA with said suction tube; and removing said delivery sheath and said isolation device.

22. The method for deploying said LAA occlusion system according to claim 20, wherein said transseptal puncture point is a fossa ovalis of said heart.

23. The method for deploying said LAA occlusion system according to claim 20, wherein said tissue forming said ostium of said LAA which said semi-permeable membrane is held to is a position selected from the list consisting of:
within said LAA; and
at said ostium of said LAA.

24. The method for deploying said LAA occlusion system according to claim 20, wherein said toxin is selected from the list consisting of:
ethanol;
a drug;
a medication;
a viral vector; and
a biological inhibitor of cellular function.

* * * * *